US012622992B2

(12) United States Patent
Valore et al.

(10) Patent No.: US 12,622,992 B2
(45) Date of Patent: May 12, 2026

(54) AIR FRESHENER WITH HINGED AND CHANNELED FRAME

(71) Applicant: Energizer Auto, Inc., St. Louis, MO (US)

(72) Inventors: Alexa Ann Valore, Cleveland, OH (US); Elin Lee LeClaire, Sheffield Village, OH (US)

(73) Assignee: Energizer Auto, Inc., St. Louis, MO (US)

( * ) Notice: Subject to any disclaimer, the term of this patent is extended or adjusted under 35 U.S.C. 154(b) by 546 days.

(21) Appl. No.: 17/944,314

(22) Filed: Sep. 14, 2022

(65) Prior Publication Data

US 2023/0080253 A1 Mar. 16, 2023

Related U.S. Application Data

(60) Provisional application No. 63/243,921, filed on Sep. 14, 2021.

(51) Int. Cl.
A61L 9/12 (2006.01)

(52) U.S. Cl.
CPC .................................... A61L 9/125 (2013.01)

(58) Field of Classification Search
CPC ...... A61L 9/12; A61L 9/125; A61L 2209/133; A61L 2209/15
USPC ...................................................... 239/54–59
See application file for complete search history.

(56) References Cited

U.S. PATENT DOCUMENTS

| | | | | |
|---|---|---|---|---|
| 8,097,214 B2 * | 1/2012 | Wood | ...................... | A61L 9/122 |
| | | | | 422/123 |
| 8,662,409 B2 * | 3/2014 | Tasz | .......................... | A61L 9/12 |
| | | | | 239/45 |
| 8,870,165 B2 * | 10/2014 | Scolari | ..................... | F04D 29/00 |
| | | | | 261/142 |
| 9,107,969 B2 | 8/2015 | Lesniak et al. | | |
| 9,474,821 B2 | 10/2016 | Lesniak et al. | | |
| 10,369,731 B2 | 8/2019 | Lesniak et al. | | |
| 10,723,051 B2 | 7/2020 | Lesniak et al. | | |
| 2004/0083640 A1 * | 5/2004 | Harris | ................. | A01M 1/2055 |
| | | | | 43/1 |
| 2007/0140923 A1 * | 6/2007 | Wiegand | ............. | A01M 1/2055 |
| | | | | 422/124 |
| 2009/0218413 A1 * | 9/2009 | Withers | ..................... | A61L 9/04 |
| | | | | 239/34 |
| 2011/0108632 A1 | 5/2011 | Brandenburg et al. | | |

FOREIGN PATENT DOCUMENTS

EP        2 022 510        *    2/2009

* cited by examiner

*Primary Examiner* — Cody J Lieuwen
(74) *Attorney, Agent, or Firm* — Lee & Hayes, P.C.

(57) ABSTRACT

An air freshener includes a first arm and a second arm connected together at one of their ends by a joint to enable swinging of the arms between an open configuration and a closed configuration. In a closed configuration, a fastener clasps opposite ends of the first arm and the second arm together to surround a central space in which a support structure, such as a support post of a rearview mirror on a vehicle, may be positioned. The first arm and the second arm each include an inner wall and lateral side walls defining an open chamber in which a fragrance substrate is retained by an interference fit. The inner wall defines an interior periphery, and ends of the lateral side walls define an exterior periphery of the air freshener.

14 Claims, 8 Drawing Sheets

AIR FRESHENER WITH HINGED AND CHANNELED FRAME

CROSS-REFERENCE TO RELATED APPLICATION

This application claims the benefit of priority of U.S. Provisional Application No. 63/243,921, entitled "Hanging Air Freshener for Securing to Rearview Mirror Support," filed Sep. 14, 2021, which is expressly incorporated herein by reference in its entirety.

TECHNICAL FIELD

The present disclosure relates generally to an air freshener configured for removable attachment to a support structure. More specifically, the present disclosure relates to an air freshener having a frame with arms hinged together at one end, channeled to confine a fragrance substrate, and openable for receiving a support structure about which the air freshener may be fastened.

BACKGROUND

In general, air convection and heat can help dissipate fragrance oils from an air freshener into an ambient space to provide an aroma. In vehicles, air fresheners are often positioned to use airflow from the ventilation system to dissipate the fragrance within the vehicle interior. For instance, the device may be placed within louvers of an air vent of the ventilation system, using forced airflow and possibly heat through the vents to disperse the fragrance. Similarly, some air fresheners have been designed to dangle from the rearview mirror, relying on movement of the vehicle and airflow from the ventilation system to help disperse the fragrance.

These designs have various drawbacks, however. Placement of an air freshener on or over vents in the vehicle can interfere with airflow within the vehicle, making the ventilation system less effective at heating or cooling the vehicle or in directing a flow of air to occupants. While not impeding an air vent, hanging air fresheners can obstruct the vision of the driver and create a distraction for the driver or passengers. Moreover, in some jurisdictions, an air freshener or other object hanging from a rearview mirror is illegal. To avoid the potential for obstructing a driver's view, other air fresheners for vehicles in the form of cans or blocks are designed to be placed under a seat. This placement also hides the device, which many users may not wish to see, but positions the air freshener far from occupants' noses, in an area of low air circulation, and in the coldest location of the vehicle interior. Because ambient heat can help disperse the fragrance oils, which must then travel a distance by diffusion to reach an occupant, under-seat air refreshers typically require a higher oil load or other accommodation to offset their deficiencies.

Achieving a balance between convection and heat within a vehicle interior for an air refresher has been difficult to achieve. While increasing temperatures and airflow can improve dispersion of fragrance oils, too much heat or too much draft can cause excessive dissipation of the fragrant material over time, shortening the life of the device or making its aroma too strong. Selective design and placement of the air freshener are needed for improved performance within a vehicle interior.

Some air fresheners for vehicles have a central longitudinal core structured as a curved and flexible I-beam that may be positioned to surround a door handle or support post of a rear view mirror. One end of the curved I-beam abuts an opposite end to form a teardrop or ring shape. A fragrance polymer is over-molded as a sleeve around the I-beam to form a rounded exterior of a substantial portion of the air freshener. The central core serves as the interior of the teardrop and, after being deformed by bending to separate the ends, can be positioned around a support structure. While intended for diverse placement in a vehicle, these I-beam air fresheners expose the fragrance polymer along a substantial portion of their exterior surface. Accordingly, the rate of diffusion cannot be controlled, and the fragrance polymer is exposed for contact by a user's hands or by materials within the vehicle. The bendable construction of the central core also can make manipulating the air freshener into place challenging, leading to undesirable contact with the exterior fragrance oils.

Examples of the present disclosure are directed to overcoming deficiencies of such systems.

SUMMARY

In an aspect of the present disclosure, air freshener includes a frame having an inner surface forming an interior periphery of the air freshener about a central space and a fragrance body including a first fragrance substrate and a second fragrance substrate. The frame includes a first frame section extending along a first inner wall between a first joint end and a first clasp end. The first frame section has a first front wall and a first rear wall extending from the first inner wall away from the central space and defining a first channel. The frame also includes a second frame section extending along a second inner wall between a second joint end and second clasp end, where the second frame section has a second front wall and a second rear wall extending from the second inner wall away from the central space to define a second channel. A joint pivotally couples the first joint end to the second joint end, and a clasp detachably connects the first clasp end to the second clasp end in a closed configuration. The first fragrance substrate has a first inner body and a first outer surface, where the first inner body is substantially enclosed within the first frame section and the first outer surface is exposed to atmosphere. The second fragrance substrate has a second inner body and a second outer surface, where the second inner body is substantially enclosed within the second frame section and the second outer surface being exposed to the atmosphere.

In another aspect of the present disclosure, a frame for an air freshener includes a first arm and a second arm. The first arm has a first inner wall extending longitudinally between a first hinge end and a first fastener end, where the first inner wall has a first interior surface. The first arm further includes a first front wall and a first rear wall extending on opposing lateral sides of the first interior surface to define a first channel. The second arm has a second inner wall extending longitudinally between a second hinge end and second fastener end, where the first hinge end are pivotally coupled to the second hinge end. The second inner wall has a second interior surface, while the second arm includes a second front wall and a second rear wall extending on opposing lateral sides of the second interior surface to define a second channel. In a closed configuration, the first fastener end is detachably connected to the second fastener end, and the first inner wall and the second inner wall form an interior periphery of the air freshener about a central space.

In yet another aspect of the present disclosure, a combination includes an air freshener and a rearview mirror of a vehicle. The air freshener includes a frame with an inner surface forming an interior periphery of the air freshener about a central space. A fragrance body includes a first fragrance substrate and a second fragrance substrate. The frame includes a first frame section extending along a first inner wall between a first joint end and a first clasp end. The first frame section has a first front wall and a first rear wall extending from the first inner wall away from the central space and defining a first channel. The frame also includes a second frame section extending along a second inner wall between a second joint end and second clasp end, where the second frame section has a second front wall and a second rear wall extending from the second inner wall away from the central space to define a second channel. A joint pivotally couples the first joint end to the second joint end, and a clasp detachably connects the first clasp end to the second clasp end in a closed configuration. The first fragrance substrate has a first inner body and a first outer surface, where the first inner body is substantially enclosed within the first frame section and the first outer surface is exposed to atmosphere. The second fragrance substrate has a second inner body and a second outer surface, where the first inner body is substantially enclosed within the second frame section and the second outer surface being exposed to the atmosphere. A support for the rearview mirror passes within the interior periphery and through the central space of the air freshener.

DETAILED DESCRIPTION

Figure 1:
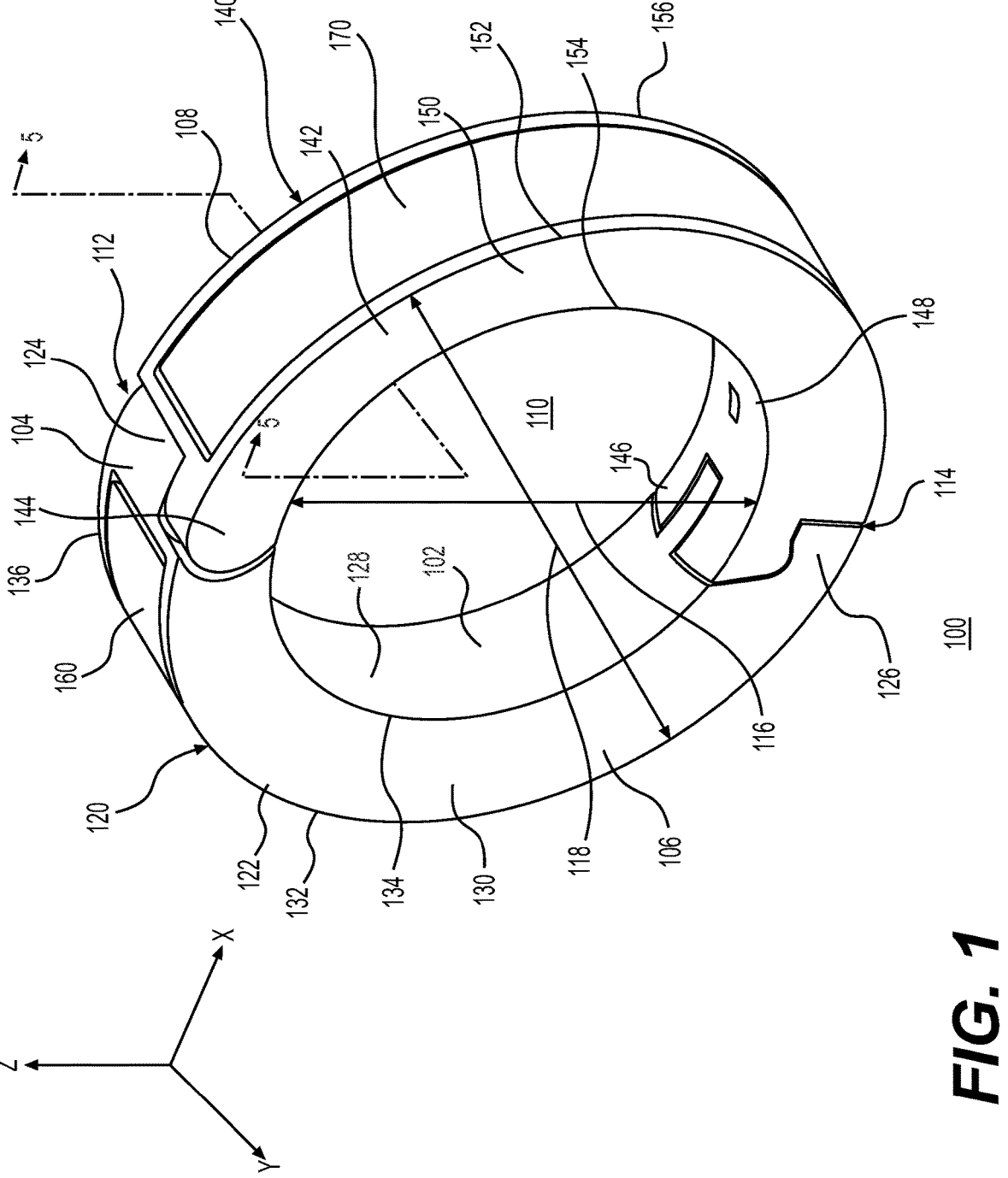
FIG. 1 is top, front, right-side isometric view of a circular air freshener in a closed configuration in accordance with an example of the present disclosure.

Wherever possible, the same reference numbers will be used throughout the drawings to refer to same or like parts.

In accordance with the principles discussed in the present disclosure, which are detailed in the following examples, an air freshener and a frame or chassis for an air freshener may include several rigid sections forming an interior periphery about a central space and which are pivotal, openable, and connectable to each other. Pivotal and openable features for the air freshener may be obtained, for example, by the several rigid sections being connected together at one of their ends by a hinge or similar structure enabling swinging of the sections between an open configuration and a closed configuration. Connectable features for the air freshener may be obtained, for example, by other ends of the several sections forming a clasp or similar fastener to become connected in a closed configuration and detached in an open configuration. In some examples, the central space, about which the several sections of the frame and the air freshener may surround, is configured to receive a support structure such as a rod or other projection. As a result, in an open configuration, the several sections of the air freshener may be moved away from each other to create a gap between the clasp, enabling the support structure to be received through the gap and into the central space. Moving the several sections together using the hinge and attaching the sections using the fastener may achieve a closed configuration in which the air freshener is detachably secured about the support structure for stable positioning and retention. In some examples, the support structure may be a support post of a rearview mirror in a vehicle.

Additionally, an air freshener consistent with the principles of the present disclosure may be configured to moderate the dissipation of fragrance oils into an ambient environment and to protect against unnecessary contact of the fragrance oils by a user. As discussed in various examples below, a frame for the air freshener may include an inner surface, a front wall, and a rear wall that collectively, in some examples, define a channel with a U-shaped or rectangular-shaped cross-section for at least partially encasing an inner body portion of a fragrance substrate having a U-shaped or a quadrilateral cross-section. As a result, in some examples, the frame may confine and hide from view and touch essentially the whole volume of the fragrance substrate. The inner wall may at least partially define an interior periphery of the frame and a central space within the air freshener. While the frame may conceal the inner body portion of the fragrance substrate, an outer surface of the fragrance substrate may be exposed to the environment and form an exterior periphery of the air freshener. The front wall and the rear wall of the frame may border the outer surface of the fragrance, further protecting the fragrance substrate from contacting surfaces of the vehicle or skin of a person.

Accordingly, when positioned on a support post of a rearview mirror, for example, an air freshener consistent with the principles of the present disclosure may be substantially hidden from view by the vehicle occupants while benefiting from increased heat at an elevated location within the vehicle interior and air flow from a defroster. As well, the frame with its channel confining the fragrance substrate can protect a user's skin from possible irritation from fragrance oils when handling the air freshener. Further, the hinge may enable the device to be readily installed and uninstalled with repeated alignment between the pivotal rigid sections at the clasp. The following describes several examples for carrying out the principles of this disclosure.

FIG. 1 illustrates a top, front, right-side isometric view of an air freshener within an XYZ coordinate system as one example consistent with the principles discussed in the present disclosure. Specifically, FIGS. 1-4 illustrate different views and components of an exemplary circular air freshener 100. FIG. 1 is a top, front, right-side view of circular air freshener 100. As generally embodied in FIG. 1, circular air freshener 100 includes an inner surface 102, an outer surface 104, a front surface 106, and a rear surface 108 arranged for reference in a position lying flat in the X-Z plane. The inner surface 102 in the example of FIG. 1 defines an interior periphery of circular air freshener 100 and generally defines a center space 110 within circular air freshener 100. As shown, center space 110 is within a boundary formed by inner surface 102 within the X-Z plane. Accordingly, as illustrated in the one example in FIG. 1, circular air freshener 100 may have a ring shape resembling a bracelet or a collar with a passageway through center space 110 along the Y axis generally through the center of the air freshener.

The circular air freshener 100 in FIG. 1 may be of any size or shape desired for a particular implementation. An inner dimension 116 and an outer dimension 118 shown in FIG. 1 help define parameters for one implementation discussed further below. In one example, inner dimension 116 is about 4 cm, and outer dimension 118 is about 8 cm. A width of outer surface 104, axially within circular air freshener 100 along the Y axis, may be about 1.5 cm in one implementation suitable for placement on a rearview mirror of a vehicle. Additionally, while the air freshener in the example of FIG. 1 is illustrated and described at times as being circular for simplicity, the shape of the air freshener may be generally round in any form, such as resembling an oval, an ellipse, or similar geometric shapes formed by having arcuate sections.

In some examples, circular air freshener 100 generally includes a left arm 120 and a right arm 140 coupled together by a joint 112 and a clasp 114. The terms "left" (toward the −X direction in FIG. 1) and "right" (toward the +X direction in FIG. 1) are used for discussion with respect to the orientation illustrated in FIG. 1, and those descriptors are not intended to be limiting to the arrangement of parts in the air freshener. For this example, left arm 120 and right arm 140 are generally arcuate in shape and, in a closed configuration for circular air freshener 100, are connected together at their ends. Shown at the top in FIG. 1, a left joint portion 124 and right joint portion 144 connect together left arm 120 and right arm 140 at joint 112. As such, left arm 120 and right arm 140 are pivotally or hingedly attached to each other. Shown at the bottom in FIG. 1, left arm 120 and right arm 140 in a closed configuration for circular air freshener 100 are detachably fastened together at opposite ends via clasp 114.

As well, left arm 120 and right arm 140 may each include a frame, namely left frame 122 and right frame 142 which are typically made of but not restricted to plastic, and a fragrance substrate, typically made of but not restricted to a polymer infused with fragrance oils. FIG. 1 depicts left fragrance substrate 160 encased or enclosed as part of left arm 120 with its exterior forming part of outer surface 104 of circular air freshener 100, and right fragrance substrate 170 retained as part of right arm 140 with its exterior also forming part of outer surface 104. The following discussion provides more detail regarding options for left frame 122, right frame 142, joint 112, clasp 114, left fragrance substrate 160, and right fragrance substrate 170 consistent with the principles of the present disclosure.

Figure 2:
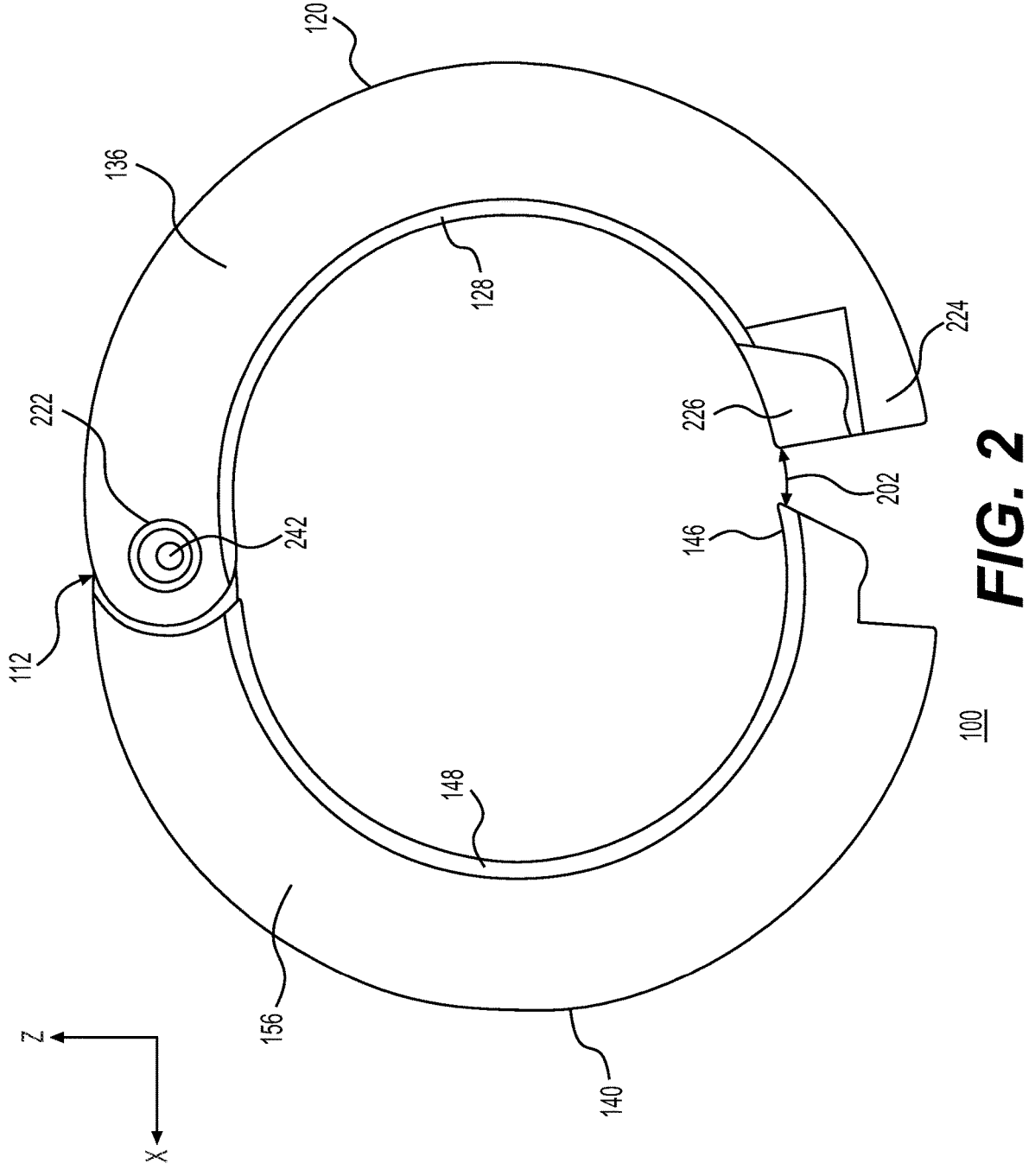
FIG. 2 is a rear view of the circular air freshener of FIG. 1 in an open configuration in accordance with an example of the present disclosure.
Figure 3:
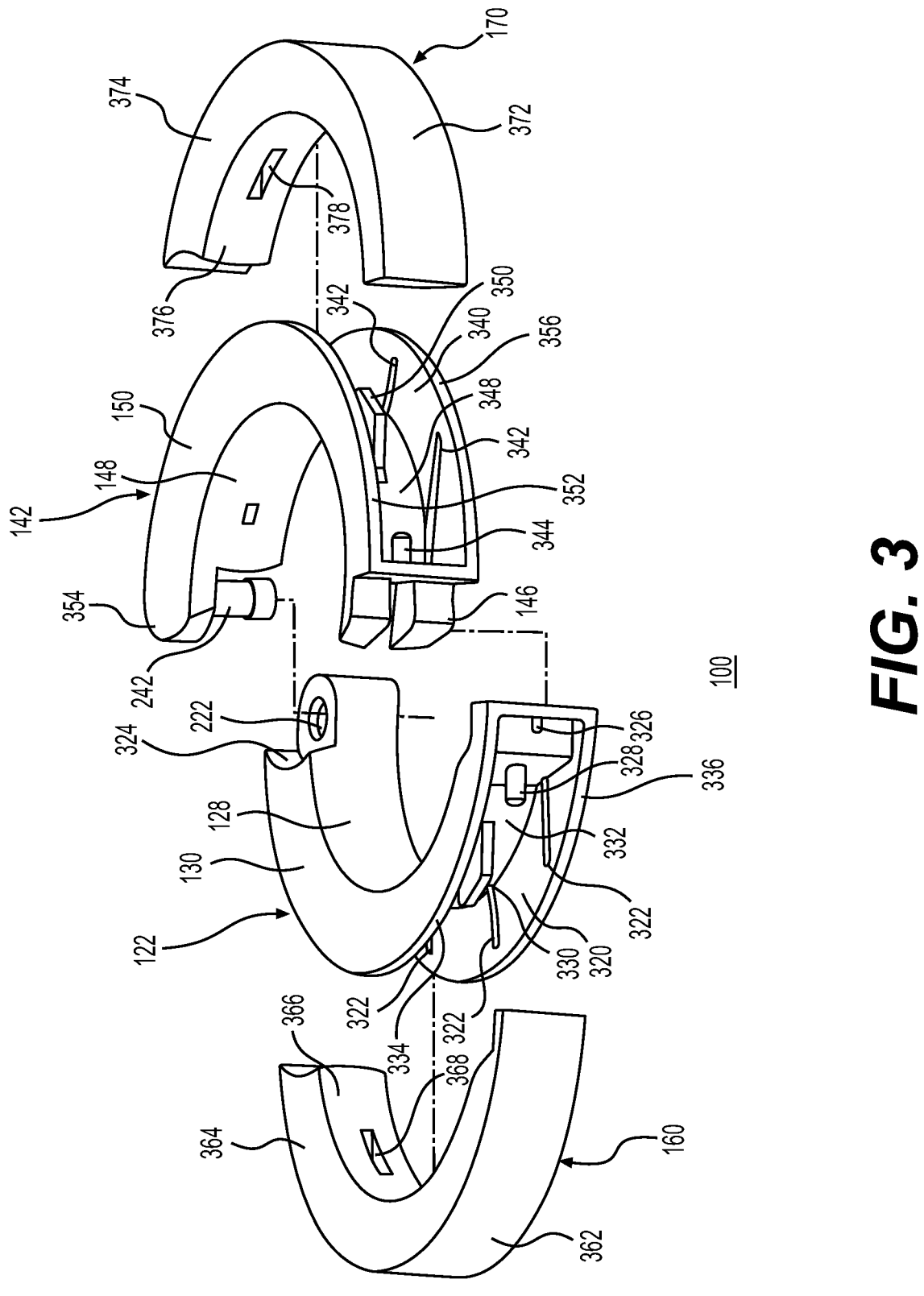
FIG. 3 is bottom, front, exploded isometric view of the circular air freshener of FIG. 1 in accordance with an example of the present disclosure.
Figure 4:
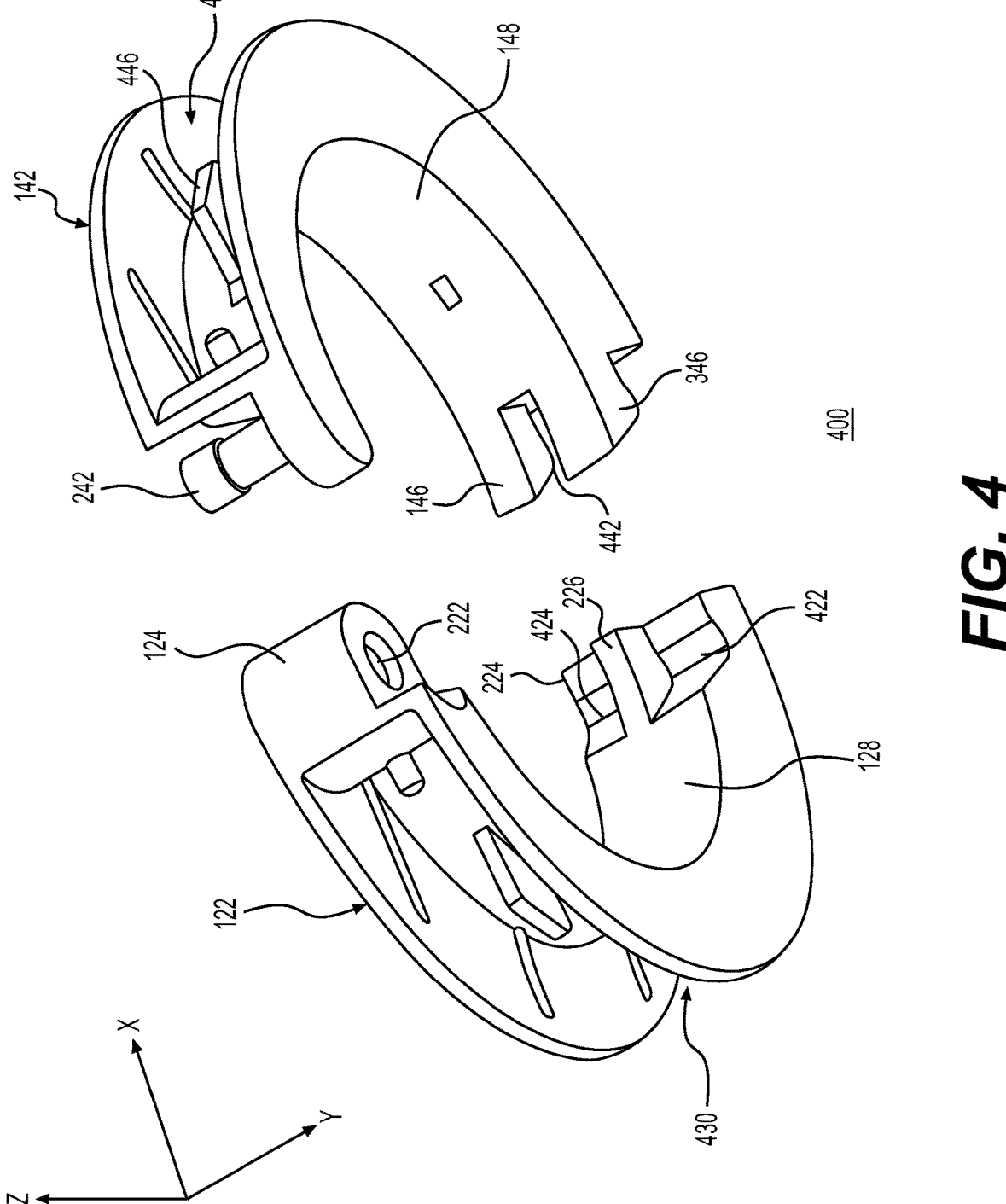
FIG. 4 is top, front exploded isometric view of a frame for a circular air freshener in accordance with an example of the present disclosure.

Referring to FIG. 1 in conjunction with FIGS. 2-4, left frame 122 in the example illustrated is an arcuate structure generally forming a channel. One example for the channel is left channel 430 and right channel 450 within frame assembly 400 shown in FIG. 4, having a substantially square-shaped cross-section extending outwardly away from center space 110. In some examples, left frame 122 has a left inner wall 128, a left front wall 130, and a left rear wall 136. On the front side, left inner wall 128 may extend to a left front inner edge 134 where it merges with left front wall 130. Left front wall 130 may extend outwardly away from center space 110 across a width defined between left front inner edge 134 and left front outer edge 132. A symmetrical structure with respect to left front wall 130 may exist for the rear side of circular air freshener 100 (not shown) to result in a substantially square-shaped cross-section the channel formed by the rigid frame, which is more clearly shown for left frame 122 in FIGS. 3 and 4.

In the example of FIG. 1, left inner wall 128, left front wall 130, and left rear wall 136 have roughly equal widths, and left inner wall 128 corresponds with inner surface 102. In other implementations, left frame 122 may have more of a V-shaped cross section with left inner wall 128 being substantially smaller in width than left front wall 130 or left rear wall 136. In yet other implementations, left frame 122 may have a rounded or U-shaped cross-section where left inner wall 128 is axially arcuate and blends into an arcuate left front wall 130 without the presence of a sharp left front inner edge 134. Other implementations may employ additional cross-sectional shapes, such as those that are rounded, pointed, or polygonal in different geometries. Left inner wall 128, as well as other outer surfaces of left frame 122, may be smooth or may be a textured. In some examples, texturing is accomplished by a pebbled or serrated surface. In other examples, texturing may be achieved by including materials providing an enhanced coefficient of friction (such as with rubber or silicone or similar material), to provide a non-slip grip when being handled by a user and to avoid shifting when in contact with a support structure.

In the example of FIG. 1, right frame 142 is a symmetrical equivalent of left frame 122. As a result, right frame 142 includes right inner wall 148, right front wall 150, right front outer edge 152, right front inner edge 154, and right rear wall 156. As well, for the example of FIG. 1, the general structure and features of right frame 142 may follow those of left frame 122 discussed above.

FIG. 3 is an exploded view of circular air freshener 100 showing the components of left arm 120, right arm 140, left fragrance substrate 160, and right fragrance substrate 170. In some examples, left frame 122 and right frame 142 are made of an oil-resistant material, such as polyoxymethylene (POM) or polypropylene, with or without additional parts of the same or different material, (e.g., acrylonitrile butadiene styrene (ABS), ceramics, or glass) or an enclosing permeable material (e.g., a woven or nonwoven fabric, paper-based, vented glass, or ceramic or perlite material). The frame may be substantially stiff and rigid, although a combination of these characteristics with materials that are flexible and resilient is possible. A rigid frame that is generally resistant to bending or deformation may provide advantages in handling the air freshener and in enabling secure or stable placement on a support structure. In some examples, left frame 122 and right frame 142 are structured to protect, encase, confine, or otherwise retain a source of fragrance, depicted in the figures as left fragrance substrate 160 within left frame 122 and right fragrance substrate 170 within right frame 142.

In one example, left fragrance substrate 160 and right fragrance substrate 170 are scented polymers, i.e., a fragrance oil mixed and compounded within a polymer. The polymer may be any suitable material commonly used in the field, such as polyvinylchloride (PVC) or ethylene-vinyl acetate (EVA). In other examples, left fragrance substrate 160 and right fragrance substrate 170 may have a base substrate material other than a polymer, such as a scented ceramic or other composition. Left fragrance substrate 160 in FIG. 3 is substantially arcuate in shape with a substantially square cross-section, having left outer surface 362, left front surface 364, and left inner surface 366. Right fragrance substrate 170 in FIG. 3 is shaped similarly, having right outer surface 372, right front surface 374, and right inner surface 376. At least left outer surface 362 and right outer surface 372 form outer surface 104 as the exterior periphery of circular air freshener 100 and are exposed to air.

It will be appreciated that left fragrance substrate 160 and right fragrance substrate 170, and the frames that confine them, may take any form desired for a particular implementation. The examples illustrated, in which left frame 122 and right frame 142 form substantially U-shaped or square-shaped cross-sections for left channel 430 and right channel 450, provide several advantages for circular air freshener 100. For instance, as discussed, the oil-resistant material walls of left frame 122 and right frame 142 help protect the fragrance oils within left fragrance substrate 160 and right fragrance substrate 170 from being handled or from contacting sensitive surfaces. FIG. 1, for example, illustrates the protection of left fragrance substrate 160 and right fragrance substrate by the frame walls.

Moreover, left front wall 130, left rear wall 136, right front wall 150, and right rear wall 156 help manage the diffusion of fragrance oils from the air freshener, shielding the bulk of the fragrance polymer from the environment but for through left outer surface 362 and through right outer surface 372. As a result, the fragrance may be slowly diffused through these outer surfaces while a remaining quantity of the fragrance polymer remains within the channels for future diffusion, potentially extending the life of the air freshener. As well, left channel 430 and right channel 450 may be configured to accommodate any desired size for left fragrance substrate 160 and right fragrance substrate 170 to balance desired rates of diffusion and length of life. In one example for an air freshener having the dimensions discussed above, fragrance oil is loaded at more than 15% by weight of a substrate made of PVC, and the combination of left fragrance substrate 160 and right fragrance substrate is at least 6 grams. Lower or higher fragrance loads may be used depending on the composition of the substrate and the desired scent intensity for the air freshener. In the present examples, the scented polymer generally surrounds center space 110, but other implementations may provide the scented polymer on a single side of center space 110 or in more than two segments.

Further, the amount, shape, and exposed areas of left outer surface 362 and right outer surface 372 of left fragrance substrate 160 and right fragrance substrate 170 may be chosen, along with the shape, color, and darkness of left frame 122 and right frame 142 to impact a desired absorption of heat and dissipation of fragrance. For instance, although generally indicated as being solid materials, left frame 122 and right frame 142 could include perforations, slits, or other discontinuities that are fixed or adjustable to help balance a desired scent intensity and duration for the air freshener. The perforations, slits, or other discontinuities may provide an increased outlet for scent diffusion from circular air freshener 100 while still shielding the inner body of left fragrance substrate 160 and right fragrance substrate 170 from being contacted.

The structure of left frame 122 and right frame 142 forming left channel 430 and right channel 450 can also enable flexible and efficient manufacturing processes. In particular, because left channel 430 and right channel 450 encase or contain left fragrance substrate 160 and right fragrance substrate 170, the fragrance substrates and the frames may be molded or otherwise formed separately and inserted together by force. More complex processes, such as injection molding the fragrance substrate as a sleeve about a core, may be avoided.

FIGS. 3 and 4 also depict internal structures of one example for left frame 122 and right frame 142. Left frame 122 includes left rear inside surface 320 and left interior surface 332 that help form a portion of left channel 430. In addition, left front wall 130 leads to left front outer wall 334, and left rear wall 136 leads to left rear outer wall 336, both of which may form a portion of outer surface 104. Left rear inside surface 320, left interior surface 332, and the inside of left front wall 130 may include various stabilizing structures configured for helping to retain left fragrance substrate 160 within left frame 122. For example, as shown in FIG. 3, left rear inside surface 320 includes one or more left ribs 322 in the form of elevated strips. Similarly, left first stabilizer 326, left second stabilizer 328, and left third stabilizer 330 can help stabilize and retain left fragrance substrate 160, particularly as left fragrance substrate 160 begins to shrink as its fragrance oils are dissipated through left outer surface 362. FIG. 3 illustrates left slot 368 where a stabilizing pin extending from left interior surface 332 may intersect left inner surface 366 of left fragrance substrate 160. When manufactured as discrete products that are assembled together, for example, a stabilizing pin from left interior surface 332 may be inserted into a corresponding slot in left fragrance substrate 160 as the components are pressed together.

Similarly, right frame 142 includes right rear outer wall 356 and right interior surface 348 as part of right channel 450, with right rear outer wall 356 having one or more right ribs 342 to assist with stabilizing right fragrance substrate 170 within right frame 142. Projections in the form of right first stabilizer 344, right second stabilizer 350, and right third stabilizer 446 (FIG. 4) may extend radially outward from right interior surface 348 to also help retain right fragrance substrate 170, particularly as it shrinks in size over time. When circular air freshener 100 is assembled, right third stabilizer 446 will be received within right slot 378 of right inner surface 376 in right fragrance substrate 170 as the components are pressed together. Right front outer wall 352 and right rear outer wall 356 may form part of outer surface 104 of the air freshener.

As discussed above, left arm 120 and right arm 140 are coupled together via joint 112 and clasp 114. Through these mechanisms, the air freshener may be positioned in a closed configuration or in an open configuration. In the closed configuration, which is shown in FIG. 1, ends of left arm 120 and right arm 140 form clasp 114, such as left clasp portion 126 and rear tongue 146 in FIG. 1, which merge together into a snap-fit connection, forming the air freshener into a closed loop. FIG. 2 is a rear view of circular air freshener 100 arranged within X-Z plane with the view facing in the Y direction. In the open configuration shown in FIG. 2, ends of left arm 120 and right arm 140 that form components of clasp 114, such as rear tongue 146 and left clasp rear portion 224 in FIG. 2, are separated from each other within the X-Z plane by a gap 202. As will be apparent, when in an open configuration, circular air freshener 100 may be inserted onto an external support structure through gap 202 so that the external support structure passes through center space 110, such as in the Y direction. When snapped together in the closed configuration, circular air freshener 100 may become stably bound around the external support structure as a collar or bracelet.

FIGS. 2-4 illustrate exemplary structures for joint 112 within left frame 122 and right frame 142. In some examples, joint 112 is a hinge. In the rear view of FIG. 2, for instance, a shaft 242 of right frame 142 is shown positioned within a socket 222 of left frame 122. In the exploded view of FIG. 3, shaft 242 is shown to be inserted when assembled into socket 222, with recess 324 providing space for the placement and rotation of right joint end 354 as shaft 242 rotates within socket 222. While joint 112 is depicted as providing rotation about the axis of shaft 242 along the Y axis in (FIGS. 1 and 2), such that left arm 120 and right arm 140 may move in the X-Z plane relative to each other, other structures and rotational axes are possible. For instance, joint 112 could be a living hinge, a ball joint, a spring-loaded hinge, or other configuration. Also, the axis for joint 112 could enable rotation of left arm 120 and right arm 140 about the X axis, for example, such that left arm 120 and right arm 140 rotate along the Y-Z plane in FIG. 1 relative to each other.

Joint 112 can enable stable and wide angular movement for left arm 120 and right arm 140. With joint 112, left arm 120 and right arm 140 may be spread farther apart, generally creating a wider gap 202 than with a singular resilient material for the frame. Moreover, joint 112 provides lateral stability for circular air freshener 100 when being moved angularly. For instance, referring to FIGS. 1 and 2, as left arm 120 and right arm 140 are rotated in the X-Z plane, joint 112 provides stability for the air freshener along the Y axis. As discussed below, this lateral stability can improve the connectedness of left arm 120 and right arm 140 within clasp 114.

In addition, when constructed of generally rigid material, joint 112, left frame 122, and right frame 142 provides a stable structure for circular air freshener 100, such that a user can rotate left arm 120 and right arm 140 between an open configuration and a closed configuration with one hand. In some examples, from a closed configuration, one finger inserted within center space 110 can force left arm 120 outward and a second finger within center space 110 can force right arm 120 outward into an open configuration. Conversely, two fingers of the same hand can readily press outwardly on left arm 120 and right arm 140, respectively, to move from an open configuration to a closed configuration.

In accordance with the principles of the present disclosure, clasp 114 may be accomplished through any structure providing temporary and detachable connection between ends of left arm 120 and right arm 140 opposite to joint 112. While FIG. 1 indicates clasp 114, FIGS. 2-4 show components of the clasp in one example as a fastener of the tongue-in-groove or dovetail style. In this option, right arm 140 includes rear tongue 146 and front tongue 346 as separate projections extending from an end of right frame 142 and separated by right clasp cavity 442 (FIG. 4). Left arm 120 includes corresponding left rear groove 424 and left front groove 422 separated by left clasp center portion 226. The tongues are shaped to fit within the grooves in clasp 114 with profiles that provide a snap fit when inserted and enable separation when pulled apart by hand. A combination of joint 112 with generally rigid material for left frame 122 and right frame 142 can enable accurate and repeatable alignment of the tongues in right arm 140 into the grooves of left arm 120. While a flexible and bendable single core for an air freshener may make alignment of the components of clasp 114 challenging, rigidity in the frame and the structure of joint 112 ensures movement of the tongue and the grooves along fixed arcs for proper alignment into a closed configuration.

The tongues or the grooves may have a textured surface or contain materials such as rubber or silicone providing an enhanced coefficient of friction to help keep clasp 114 fastened in the closed position. While shown as coming together and separating along the X-Z plane, the tongues and grooves of clasp 114 could be configured to interact instead along the Y-Z plane depending on the rotational axis chosen for joint 112. Clasp 114 may be implemented in a variety of options, including male/female fittings, hooks, catches, sliding gates, keyhole fittings, twist clasps, magnets, spring-loaded clips, and similar structures.

Figure 5:
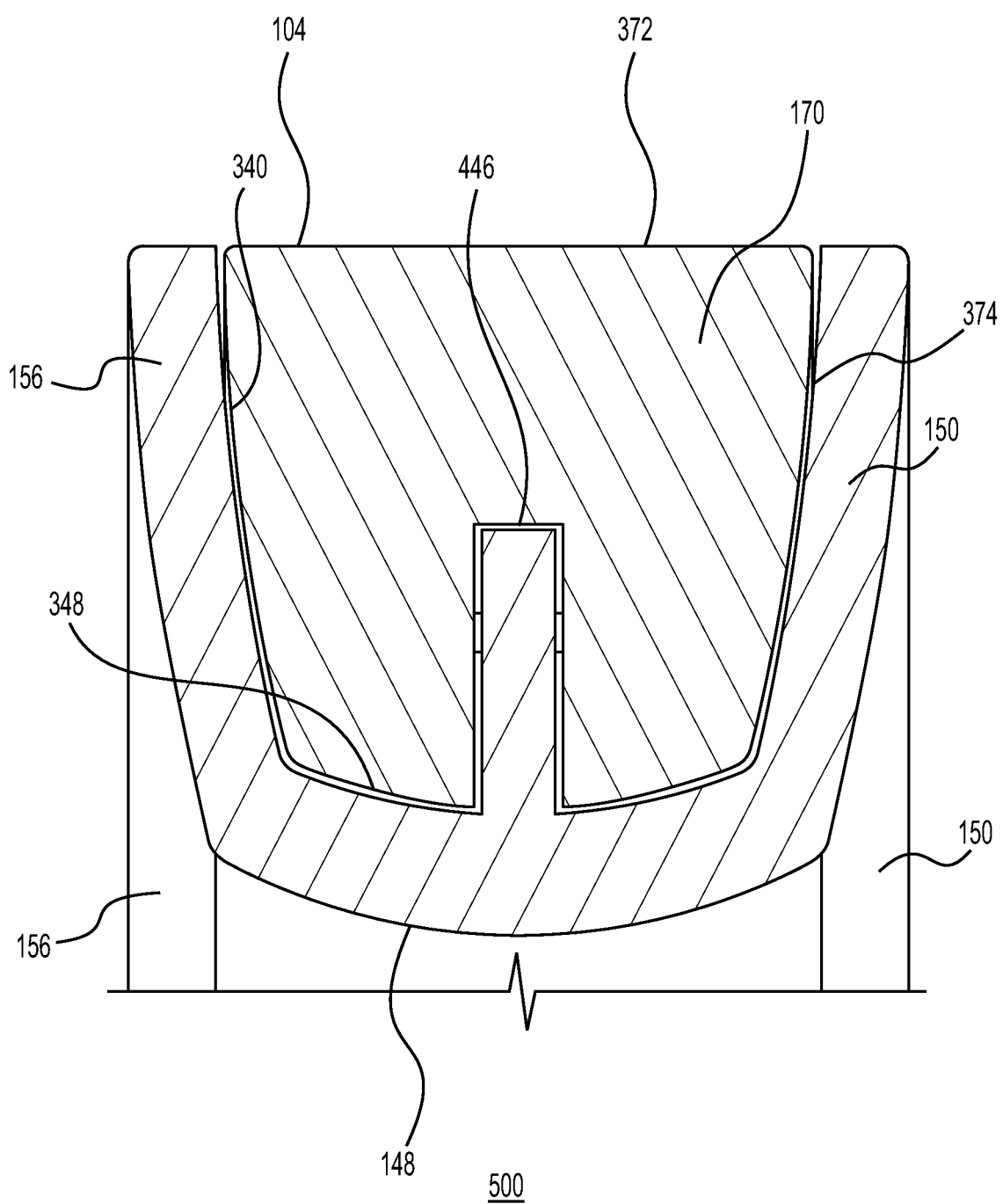
FIG. 5 is a radial sectional view of the circular air freshener along cutaway lines of FIG. 1 in accordance with an example of the present disclosure.

Referring to FIG. 5, a radial cross section of right arm 500 is illustrated based on cutaway lines indicated in FIG. 1. The right side of FIG. 5 shows right front wall 150, while the left side shows right rear wall 156. The cutaway is made to bisect right third stabilizer 446, which extends radially outward from right interior surface 348 and into right fragrance substrate 170. Intersecting with right fragrance substrate 170, right third stabilizer 446 provides stability and some retention for right fragrance substrate 170 within right channel 450 formed by right front wall 150 and right rear wall 156 as the fragrance material is dissipated. Without stabilizing structures, such as 426, right fragrance substrate 170 may become detached from right frame 142 as it shrinks from dissipation. FIG. 5 also indicates for one example the shape of right channel 450, having slightly angled side walls such as right inside wall 340 and slightly curved right interior surface 348, within the scope of the discussion above of a substantially square-shaped cross-section of right frame 142. As a result, the cross-section of the right channel 450 and right fragrance substrate 170 may be viewed as a quadrilateral.

As illustrated in FIG. 5, right fragrance substrate 170 may be inserted within right channel 450 to generate a tight fit, or an interference fit, within right frame 142. Although a volume of right fragrance substrate 170 will decrease over time as the fragrance oils dissipate into the atmosphere, in some examples, an initial volume of right fragrance substrate 170 substantially corresponds with a volume of the space within right channel 450, as shown in FIG. 5. In that example, right outer surface 372 would be essentially flush, or co-planar with, and bounded by right front outer edge 152 and the outer edge of right rear wall 156. In some examples, the initial volume of right fragrance substrate 170 may be less than the volume of the space within right channel 450, such that the radial height of right outer surface 372 is less than the radial height of right front wall 150 and right rear wall 156, i.e., right outer surface 372 is recessed below right front outer edge 152. In this way, right fragrance substrate 170 may be further withdrawn from incidental contact by a user's hands or surrounding materials and guarded by both the sides and the outer edges or ends of right front wall 150 and right rear wall 156. Accordingly, for this option, the outer surfaces of front and rear walls, e.g., right front wall 150 and right rear wall 156, become the outer surface 104 for circular air freshener 100.

Figure 6:
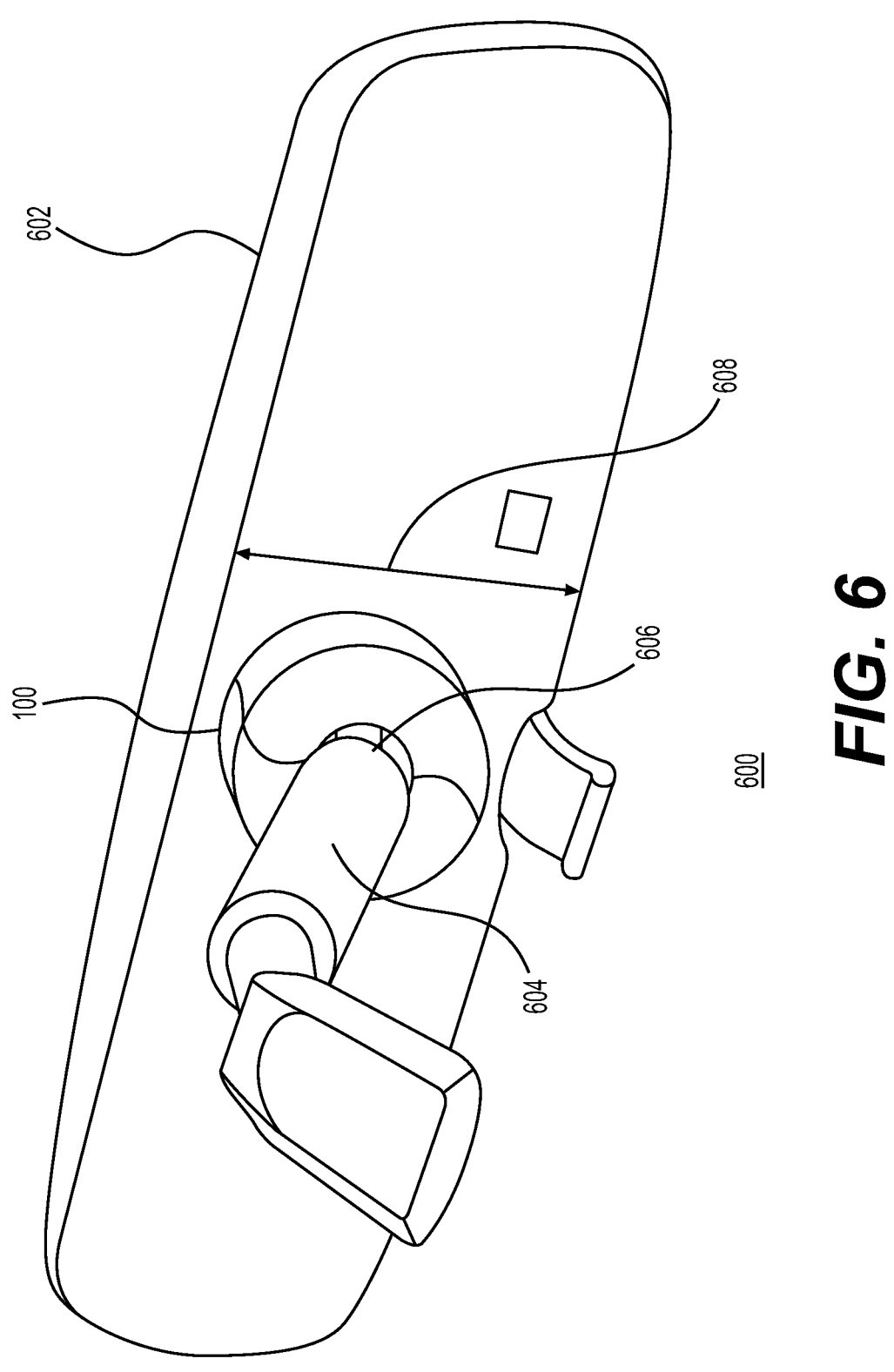
FIG. 6 is a rear, left-side isometric view of a circular air freshener in a closed configuration on a rearview mirror of a vehicle in accordance with an example of the present disclosure.

Turning to FIG. 6, air freshener installation 600 depicts an exemplary circular air freshener 100 positioned on the back side of a rearview mirror 602 within the interior of a vehicle. For circular air freshener 100 to be installed, a user would pull left arm 120 and right arm 140 away from each other so that they pivot about joint 112, which due to the generally rigid structure for left frame 122, right frame 142, and joint 112 can in some examples be accomplished readily with one hand. If circular air freshener 100 had been in a closed configuration, pulling apart the arms would cause rear tongue 146 and front tongue 346 of clasp 114 to become detached from left rear groove 424 and left front groove 422. As indicated in FIG. 2, gap 202 would form within clasp 114, through which circular air freshener 100 could be slid onto support 604. In some examples suitable for use on a rearview mirror, inner dimension 116 would be sufficiently larger than a support width 606 of the apparatus supporting rearview mirror 602. In addition, in some examples, outer dimension 118 would be less than or equal to body height 608 of rearview mirror 602 to conceal the air freshener from view within the vehicle.

When installed as shown in FIG. 6, circular air freshener 100 may provide several advantages. For instance, the rearview mirror in a vehicle is high within the interior, at a location where heat will naturally rise and help facilitate dispersion of fragrance oils from left fragrance substrate 160 and right fragrance substrate 170. Fragrance dispersion may also be enhanced by heat radiation from sunlight passing through the windshield and striking the back side of rearview mirror 602. In some examples, front and rear walls of the frame may be darkened to enhance heat absorption. Further, forced air from the defroster of the ventilation system may be used—purposedly or incidentally—to help dissipate the fragrance oils by convection. On the other hand, having a substantial portion of left fragrance substrate 160 and right fragrance substrate 170 enclosed within left frame 122 and right frame 142 with external exposure through left outer surface 362 and right outer surface 372 may help to slow excessive dissipation of the fragrance oils, as well as to ensure safe handling of the air freshener without excess contact with the scented polymer. In addition, locating circular air freshener 100 at the back side of rearview mirror 602 with outer dimension 118 being less than body height 608 will conceal circular air freshener 100 from view by occupants of the vehicle.

Fragrance dispersion may be further controlled in some examples through adjustment of the structure and characteristics for left frame 122 and right frame 142. For instance, making left frame 122 and right frame 142 opaque or reflective to help block access of light radiation to left fragrance substrate 160 and right fragrance substrate 170 can lead to less diffusion of the fragrance. On the other hand, using materials for the frames that are translucent may help increase light access and result in more scent diffusion from the same fragrance substrate, while still minimizing external contact with fragrance oils. Alternatively, including perforations or other discontinuities within left frame 122 and right frame 142 may also increase diffusion through increased access to the fragrance substrate by radiation, such as from sunlight through a vehicle windshield, or by air flow, such as from a vehicle defroster.

Figure 7:
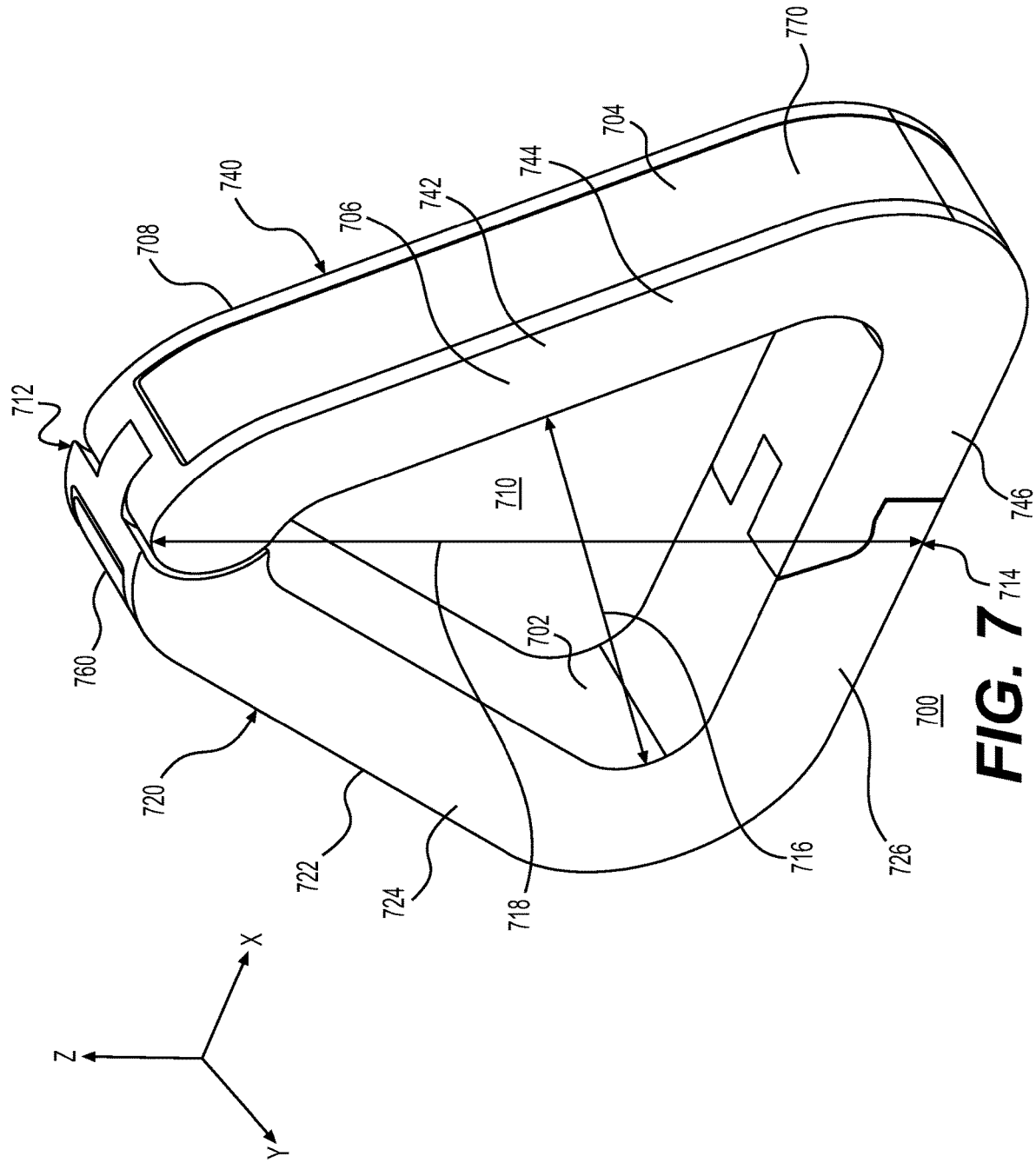
FIG. 7 is top, front, right-side isometric view of a triangular air freshener in a closed configuration in accordance with an example of the present disclosure.
Figure 8:
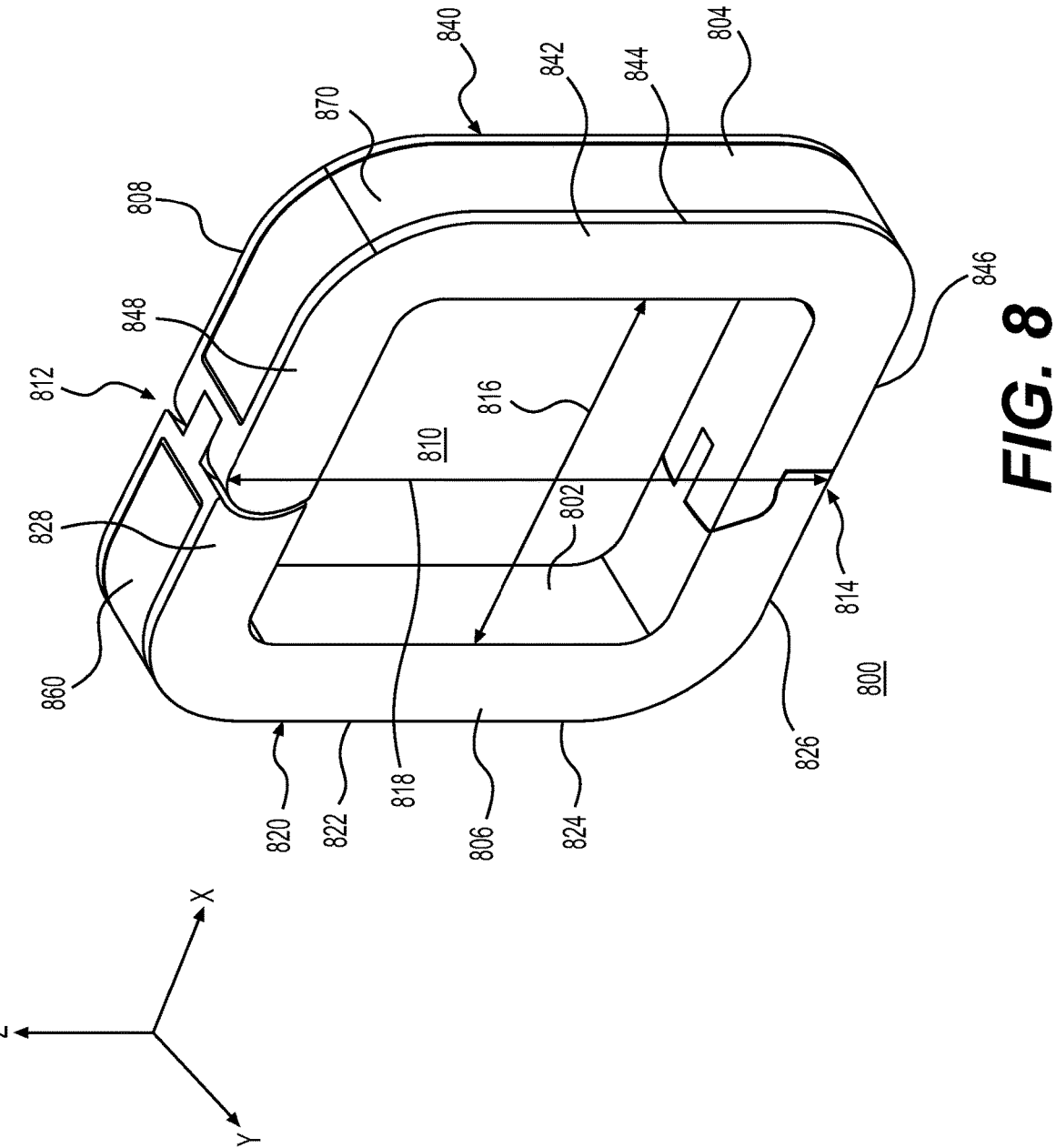
FIG. 8 is top, front, right-side isometric view of a rectangular air freshener in a closed configuration in accordance with an example of the present disclosure.

While circular air freshener 100 has been described as a structure with exterior periphery substantially formed by outer surface 104 and interior periphery substantially formed by inner surface 102 both having an overall round shape (whether circular, oval, elliptical, or other curved variation), some examples consistent with the present disclosure may differ from roundness. For example, while not illustrated, some examples of circular air freshener 100 could have a round or circular shape to outer surface 104 about center space 110, while inner surface 102 forms a different geometric shape for the interior periphery about center space 110. For instance, outer surface 104 could be substantially round, while inner surface 102 is substantially polygonal or other form. Also, while the forms of outer surface 104 and inner surface 102 have been discussed as being generally symmetrical about center space 110, either inner surface 102 or outer surface 104 may be asymmetrical. FIGS. 7 and 8 illustrate further examples for an air freshener having a joint and a clasp with different shapes within the principles of the present disclosure.

FIG. 7 depicts an attachable air freshener with a hinge joint and a clasp having a substantially triangular shape. For simplicity, the triangular air freshener 700 has the same or similar structure as circular air freshener 100 for purposes of illustration. In particular, triangular air freshener 700 has an inner surface 702, an outer surface 704, a front surface 706, and a rear surface 708 that forms the boundaries of its structure. The inner surface 702, which is triangular in the illustrated example but may take any shape, defines center space 710 for receiving an external support structure through the interior of the air freshener. Triangular air freshener 700 may be divided into two sections: left arm 720 and right arm 740 connected in a closed configuration by joint 712 and clasp 714. Triangular air freshener 700 has an inner dimension 716 and an outer dimension 716, generally defined as the maximum distances across inner surface 702 and outer surface 704, respectively.

Turning to the components within triangular air freshener 700, similar to circular air freshener 100, triangular air freshener 700 includes left arm 720 formed by left fragrance substrate 760 having an inner body substantially encased within left frame 722. Likewise, right arm 740 is formed by right fragrance substrate 770 having an inner body substantially encased within right frame 742. Left frame 722 includes left side portion 724 and left bottom portion 726. While referred to as being in common with left arm 720, left side portion 724 and left bottom portion 726 may also be viewed as subsections within triangular air freshener 700. On the right side, right frame 742 includes right side portion 744 and right bottom portion 746. Joint 712 and clasp 714 in some examples function similarly to joint 112 and clasp 114 in FIGS. 1-4, by dividing triangular air freshener 700 into two halves that may pivot apart into an open configuration and pivot and snap together in a closed configuration. Although not shown, joint 712 and clasp 714 need not be positioned to divide triangular air freshener 700 in half and may be placed elsewhere within triangular air freshener 700. For instance, in some examples, joint 712 and clasp 714 could be located within the same side of triangular air freshener 700, such as at opposite ends of left side portion 724.

As discussed above for circular air freshener 100, triangular air freshener 700 may deviate from exact geometry of a triangle, for example, for inner surface 702 and outer surface 704. While triangular air freshener 700 is shown essentially as an equilateral triangle, other triangular shapes are contemplated, such as isosceles and right triangles. Moreover, the shape defined about center space 710 by inner surface 702 may be different from a triangle, such as round or square, while outer surface 704 is a triangle, and vice versa.

FIG. 8 depicts another example of an attachable air freshener with a hinge joint and a clasp having a substantially rectangular shape. For simplicity, the rectangular air freshener 800 has the same or similar structure as circular air freshener 100 for purposes of illustration. In particular, rectangular air freshener 800 has an inner surface 802, an outer surface 804, a front surface 806, and a rear surface 808 that forms the boundaries of its structure. The inner surface 802, which is rectangular in the illustrated example but may take any shape, defines center space 810 for receiving an external support structure through the interior of the air freshener. Rectangular air freshener 800 may be divided into two sections: left arm 820 and right arm 840 connected in a closed configuration by joint 812 and clasp 814. Rectangular air freshener 800 has an inner dimension 816 and an outer dimension 818, generally defined as the maximum distances across inner surface 802 and outer surface 804, respectively.

Rectangular air freshener 800 includes left arm 820 formed by left fragrance substrate 860 having an inner body substantially encased within left frame 822. Likewise, right arm 840 is formed by right fragrance substrate 870 having an inner body substantially encased within right frame 842. Left frame 822 includes left side portion 824, left bottom portion 826, and left top portion 828. While referred to as being in common arm with left arm 820, left side portion 824, left bottom portion 826, and left top portion 828 may also be viewed as subsections within rectangular air freshener 800. On the right side, right frame 842 includes right side portion 844, right bottom portion 846, and right top portion 848. Joint 812 and clasp 814 in some examples function similarly to joint 112 and clasp 114 in FIGS. 1-4, by dividing rectangular air freshener 800 into two halves that may pivot apart into an open configuration and pivot and snap together in a closed configuration. Although not shown, joint 812 and clasp 814 need not be positioned to divide rectangular air freshener 800 in half and may be placed elsewhere within rectangular air freshener 800. For instance, in some examples, joint 812 and clasp 814 could be located at opposite corners of rectangular air freshener 800. In other possibilities, joint 812 and clasp 814 could be located within the same side of rectangular air freshener 800, such as at opposite ends of left side portion 824. Other variations for the arrangement of joint 812 and clasp 814 are also possible.

Rectangular air freshener 800 may deviate from the exact geometry illustrated. For instance, while rectangular air freshener 800 is shown essentially as a square, other polygonal shapes are contemplated, such as rectangles, hexagons, rhombuses, trapezoids, etc. Moreover, the shape defined about center space 810 by inner surface 802 may be different from a rectangle, such as round or triangular, while outer surface 804 is a rectangle, and vice versa.

Accordingly, an air freshener consistent with the principles of this disclosure may provide a flexible arrangement adaptable for attachment to any rod or projection, such as a support post of a rearview mirror in a vehicle. The joint can enable a wide gap in an open configuration for installing the air freshener, and the clasp ensures retention of the air freshener in a closed configuration about the rod or projection, as with a collar or bracelet. The frame for the air freshener may permit encapsulation of a fragrance substrate within a channel while exposing a surface of the substrate to air at an exterior periphery of the air freshener, which can help control dissipation of fragrance oils for concentration and duration and help protect the fragrance substrate from contact by surrounding surfaces or skin. When installed on the support post of rearview mirror, the air freshener can be hidden from view of the vehicle occupants, while benefiting from the increased heat at an elevated position within the vehicle and from sunlight entering the windshield. As well, the ventilation system of the vehicle may be used in defrost mode to help diffuse fragrance from the air freshener as desired.

Those of ordinary skill in the field will appreciate that the principles of this disclosure are not limited to the specific examples discussed or illustrated in the figures. For example, while circular air freshener 100, triangular air freshener 700, and rectangular air freshener 800 have been discussed in the context of attachment to a support structure for a rearview mirror of a vehicle due to the advantages addressed, the air fresheners may be attached to any suitable structure in any location. For instance, the air fresheners may be clipped to a gear shift, a headrest bar, a grab handle, seat positioning bar, or any other projection of suitable size within a vehicle. In addition, the principles disclosed are not limited to implementation in an interior of a vehicle. Any space deriving benefit from air fragrance could benefit from the examples and techniques disclosed and claimed. Moreover, while the present disclosure addresses air fresheners with frames having certain identified shapes, the shape or form of the air freshener containing joint 112 and clasp 114 is not limiting.

Unless explicitly excluded, the use of the singular to describe a component, structure, or operation does not exclude the use of plural such components, structures, or operations or their equivalents. As used herein, the word "or" refers to any possible permutation of a set of items. For example, the phrase "A, B, or C" refers to at least one of A, B, C, or any combination thereof, such as any of: A; B; C; A and B; A and C; B and C; A, B, and C; or multiple of any item such as A and A; B, B, and C; A, A, B, C, and C; etc.

Terms of approximation are meant to include ranges of values that do not change the function or result of the disclosed structure or process. For instance, the term "about" generally refers to a range of numeric values that one of skill in the art would consider equivalent to the recited numeric value or having the same function or result. Similarly, the antecedent "substantially" means largely, but not wholly, the same form, manner or degree, and the particular element will have a range of configurations as a person of ordinary skill in the art would consider as having the same function or result. As an example, "substantially parallel" need not be exactly 180 degrees but may also encompass slight variations of a few degrees based on the context.

While aspects of the present disclosure have been particularly shown and described with reference to the embodiments above, it will be understood by those skilled in the art that various additional embodiments may be contemplated by the modification of the disclosed systems and methods without departing from the spirit and scope of what is disclosed. Such embodiments should be understood to fall within the scope of the present disclosure as determined based upon the claims and any equivalents thereof.

What is claimed is:

1. An air freshener, comprising:

a frame having an inner surface forming an interior periphery of the air freshener about a central space, the central space defining a passageway along an axis through the air freshener for receiving an external support structure, the frame comprising:

a first frame section extending along a first inner wall between a first joint end and a first clasp end, the first inner wall forming a first portion of an outer boundary of the central space and having a first interior surface, the first frame section having a first front wall and a first rear wall extending radially from the first inner wall away from the central space and defining a first channel, the first front wall culminating in a first front outer edge along the first channel, the first rear wall culminating in a first rear outer edge along the first channel, the first front outer edge and the first rear outer edge being axially separated by a first distance open to atmosphere, a second frame section extending along a second inner wall between a second joint end and second clasp end, a joint pivotally coupling the first joint end to the second joint end, and a clasp detachably connecting the first clasp end to the second clasp end in a closed configuration; and

a first fragrance substrate having a first inner body and a first outer surface, the first inner body being substantially enclosed within the first frame section, the first outer surface being radially outward from the first interior surface of the first inner wall and being exposed to the atmosphere across the first distance in the closed configuration, wherein the first outer surface of the first fragrance substrate forms an exterior periphery of the air freshener along the first channel radially outward from the interior periphery.

2. The air freshener of claim 1, wherein the second inner wall forms a second portion of the outer boundary of the central space and has a second interior surface, the second frame section having a second front wall and a second rear wall extending radially from the second inner wall away from the central space and defining a second channel, the second front wall culminating in a first front outer edge along the second channel, the second rear wall culminating in a second rear outer edge along the second channel, the second front outer edge and the second rear outer edge being axially separated by a second distance open to the atmosphere across the second distance in the closed configuration.

3. The air freshener of claim 2, further comprising:

a second fragrance substrate having a second inner body and a second outer surface, the second inner body being substantially enclosed within the second frame section, the second outer surface being radially outward from the second interior surface of the second inner wall and being exposed to the atmosphere across the second distance, wherein the second outer surface of the second fragrance substrate forms the exterior periphery of the air freshener along the second channel radially outward from the interior periphery.

4. The air freshener of claim 1, wherein the first outer surface of the first fragrance substrate is co-planar with the first front outer edge and the first rear outer edge.

5. The air freshener of claim 1, wherein the first frame section shields the first fragrance substrate from the environment except through the first outer surface.

6. The air freshener of claim 1, wherein the first joint end contains a shaft, the second joint end contains a socket, and the shaft is positioned within the socket.

7. The air freshener of claim 6, wherein the first clasp end contains a tongue, the second clasp end contains a groove, and the tongue is positioned within the groove in the closed configuration.

8. The air freshener of claim 1, wherein a substrate volume of the first fragrance substrate is less than or equal to a channel volume of a space within the first channel.

9. The air freshener of claim 1, wherein the first front wall and the first rear wall extend radially beyond the first outer surface of the first fragrance substrate.

10. The air freshener of claim 9, wherein the first front wall and the first rear wall extend between the interior periphery and the exterior periphery of the air freshener.

11. The air freshener of claim 1, wherein a cross-section of the first fragrance substrate is substantially a quadrilateral.

12. The air freshener of claim 1, further comprising one or more first ribs on one of the first front wall and the first rear wall within the first channel, the one or more first ribs being configured to stabilize the first fragrance substrate within the first frame.

13. The air freshener of claim 1, wherein the first channel includes one or more stabilizing projections extending radially outward from the first interior surface and intersecting with the first fragrance substrate.

14. A combination, comprising:

a frame having an inner surface forming an interior periphery of the air freshener about a central space, the central space defining a passageway along an axis through the air freshener for receiving an external support structure, the frame comprising:

a first frame section extending along a first inner wall between a first joint end and a first clasp end, the first inner wall forming a first portion of an outer boundary of the central space and having a first interior surface, the first frame section having a first front wall and a first rear wall extending radially from the first inner wall away from the central space and defining a first channel, the first front wall culminating in a first front outer edge along the first channel, the first rear wall culminating in a first rear outer edge along the first channel, the first front outer edge and the first rear outer edge being axially separated by a first distance open to atmosphere, a second frame section extending along a second inner wall between a second joint end and second clasp end, a joint pivotally coupling the first joint end to the second joint end, and a clasp detachably connecting the first clasp end to the second clasp end in a closed configuration, a first fragrance substrate having a first inner body and a first outer surface, the first inner body being substantially enclosed within the first frame section, the first outer surface being radially outward from the first interior surface of the first inner wall and being exposed to the atmosphere across the first distance in the closed configuration, wherein the first outer surface of the first fragrance substrate forms an exterior periphery of the air freshener along the first channel radially outward from the interior periphery; and a rearview mirror of a vehicle, the rearview mirror having a body and a support, wherein the support of the rearview mirror passes within the interior periphery and through the central space of the air freshener.

* * * * *